United States Patent [19]

Hoshino et al.

[11] Patent Number: 5,312,741
[45] Date of Patent: May 17, 1994

[54] PROCESS FOR PRODUCING 2-KETO-L-GULONIC ACID

[75] Inventors: Tatsuo Hoshino, Kamakura; Setuko Ojima, Fujisawa; Teruhide Sugisawa, Yokohama, all of Japan

[73] Assignee: Hoffmann-La Roche Inc., Nutley, N.J.

[21] Appl. No.: 895,289

[22] Filed: Jun. 8, 1992

[30] Foreign Application Priority Data

Jun. 13, 1991 [EP] European Pat. Off. ........ 91810451.4

[51] Int. Cl.$^5$ .......................... C12P 7/60; C12P 39/00; C12N 1/20; C12R 1/38
[52] U.S. Cl. ..................... 435/42; 435/138; 435/822; 435/823
[58] Field of Search .............. 435/42, 138, 822, 823

[56] References Cited

U.S. PATENT DOCUMENTS

| Re. 30,872 | 2/1982 | Sonoyama et al. | 435/138 |
| 4,892,823 | 1/1990 | Imai et al. | 435/138 |
| 4,933,289 | 6/1990 | Imai et al. | 435/138 |
| 4,935,359 | 6/1990 | Yin et al. | 435/138 |
| 4,960,695 | 10/1990 | Hoshino et al. | 435/42 |

FOREIGN PATENT DOCUMENTS

| 213591 | 3/1987 | European Pat. Off. | 435/138 |
| 0221707 | 5/1987 | European Pat. Off. | 435/42 |
| 3112989 | 5/1988 | Japan | 435/138 |

OTHER PUBLICATIONS

Isono et al., Agr. Biol. Chem. 35:424–431 (1968).
Sugisawa et al., Agr. Biol. Chem. 54:1201–1209 (1990).

*Primary Examiner*—Herbert J. Lilling
*Attorney, Agent, or Firm*—George M. Gould; William H. Epstein; Catherine P. Roseman

[57] ABSTRACT

The present invention relates to a process for producing 2-keto-L-gulonic acid by fermentative conversion of D-sorbitol in high yield. 2-Keto-L-gulonic acid is an important intermediate for the production of L-ascorbic acid into which it can be converted.

18 Claims, No Drawings

PROCESS FOR PRODUCING 2-KETO-L-GULONIC ACID

BACKGROUND OF THE INVENTION

2-Keto-L-gulonic acid is an important intermediate for the production of L-ascorbic acid, into which it can be converted.

The production of 2-keto-L-gulonic acid from L-sorbose or from D-sorbitol by fermentation is known.

As to L-sorbose, as disclosed in "Acta Microbiologica Sinica" 21(2), 185-191 (1981), 2-keto-L-gulonic acid can be produced from L-sorbose by a mixed culture of microorganisms, specifically Pseudomonas striata and Gluconobacter oxydans. The yield of this process is 30 g/l from a starting concentration of 70 g/l of L-sorbose. and 37 g/l from a starting concentration of 100 g/l of L-sorbose. European Patent Publication No. 0221 707 discloses the production of 2-keto-L-gulonic acid from L-sorbose by Pseudogluconobacter saccharoketogenes with and without concomitant bacteria. However, the yield of this process using Pseudogluconobacter saccharoketogenes is at most 55.3-87.6 g/l (conversion ratio: 34.2-54.1%)(See:page 13, Table 4 of European Patent Publication No. 0221 707). European Patent Publication No. 0278 447 discloses a process for the production of 2-keto-L-gulonic acid from L-sorbose by a mixed culture of microorganisms, one of which has the identifying characteristics of strain DSM No. 4025 and the other of which has the identifying characteristics of DSM No. 4026 (a Bacillus megaterium strain). The yield of this process is at least 40 g/l.

As to D-sorbitol, Japanese Patent Publication No. 40154/1976 discloses the production of 2-keto-L-gulonic acid from D-sorbitol by microorganisms of the genus Acetobacter, Bacterium or Pseudomonas. These microorganisms are capable of oxidizing D-sorbitol under aerobic condition producing 2-keto-L-gulonic acid. This process gives a low yield of less than 6 g/l. D-sorbitol as a starting material would be preferable to L-sorbose because it is less costly. However, the yield of 2-keto-L-gulonic acid from D-sorbitol is low.

The above processes represent attempts to microbiologically produce 2-keto-L-gulonic acid directly from either L-sorbose or D-sorbitol as starting materials. However due to the relatively low yields these processes are far from an industrial scale of production, especially when D-sorbitol is the starting material.

On the other hand, the fermentative production of L-sorbose from D-sorbitol is known. Various Acetobacter (presently classified into Gluconobacter) strains such as Acetobacter xylinum and Acetobacter suboxydans are known to produce L-sorbose from D-sorbitol efficiently (Biotechnology, volume 6a, 436-437, 1984, edited by H.-J. Rehm and G. Reed, published by Verlag Chemie, Weinheim, Germany). D-Sorbitol is a less costly material than L-sorbose, but L-sorbose is more efficiently converted to 2-keto-L-gulonic acid. Therefore, a process that uses D-sorbitol as a starting material, but provides L-sorbose for conversion, combines the availability of D-sorbitol with the higher yield provided by L-sorbose. If part of the process is the conversion of D-sorbitol to L-sorbose, which is then converted to 2-keto-L-gulonic acid, then efficient production will be attained.

Provided that one can establish an efficient production process of 2-keto-L-gulonic acid starting from a cheaper carbon source such as D-sorbitol rather than from L-sorbose, it is obvious that production will be dramatically simplified.

SUMMARY OF THE INVENTION

The present invention relates to a process for producing 2-keto-L-gulonic acid with a mixture of microorganisms by fermentative conversion of D-sorbitol in high yield. The present process enables yields of at least ca. 60 g/l, and yields of ca. 130 g/l are achievable.

DETAILED DESCRIPTION OF THE INVENTION

The strain DSM No. 4025 is capable of producing 2-keto-L-gulonic acid from L-sorbose efficiently as mentioned above, whereas it gives low conversion yield from D-sorbitol. The low conversion yield of 2-keto-L-gulonic acid from D-sorbitol is due to the formation of by-products such as D-glucose, D-gluconate and 2-keto-D-gulonic acid derived from D-sorbitol. The purification of 2-keto-L-gulonic acid from its isomer, 2-keto-D-gluconic acid, results in difficulties. A possible metabolic pathway of D-sorbitol in the strain DSM No. 4025 is shown below.

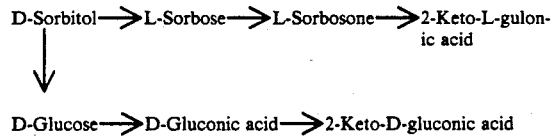

Improving the yield of 2-keto-L-gulonic acid from D-sorbitol in the fermentation using strain DSM No. 4025 can be attained by strengthening the L-sorbose formation pathway as much as possible, as described herein. It is therefore an object of the present invention to provide a novel method for preparing 2-keto-L-gulonic acid from D-sorbitol in high conversion yield, e.g. at least ca. 50 mol % and up to conversion yields of ca. 89 mol %.

Another object of the present invention is to provide a mode of operation wherein the production of undesired by-products such as D-glucose, D-gluconic acid and 2-keto-D-gluconic acid is prevented.

The present invention is concerned with a process for producing 2-keto-L-gulonic acid or a salt thereof, which comprises cultivating a mixed culture of a first microorganism (A) capable of producing L-sorbose from D-sorbitol, which belongs to the genus Gluconobacter or Acetobacter, and a second microorganism (B) capable of producing 2-keto-L-gulonic acid from L-sorbose and having the identifying characteristics of the strain DSM No. 4025, a functional equivalent, subculture, mutant or variant thereof, in a medium containing D-sorbitol, whereby mixed culturing is conducted, wherein both of said microorganisms are coexisting in the medium during at least part of the entire cultivation period, and recovering the 2-keto-L-gulonic acid or a salt thereof. Culturing in the medium continues for a period of time sufficient for the production of 2-keto-L-gulonic acid from D-sorbitol.

L-sorbose produced from D-sorbitol by the L-sorbose producing strain can be used by the 2-keto-L-gulonic acid producing strain to form 2-keto-L-gulonic acid. The accumulation of by-products is not substantially observed in this process.

Any microorganism capable of converting D-sorbitol to L-sorbose may be used in this invention, in combination with any microorganism capable of converting L-sorbose to 2-keto-L-gulonic acid and having characteristics substantially similar to those of DSM No. 4025.

Microorganism (A) capable of producing L-sorbose from D-sorbitol employed herein belongs to the genus Gluconobacter or Acetobacter. Microorganism (B) capable of producing 2-keto-L-gulonic acid from L-sorbose has the identifying characteristics of the strain DSM No. 4025, or a functional equivalent, subculture, mutant or variant thereof.

In the instant process, any products resulting from treating the cells of the microorganisms (A) and (B), for instance, resting cells, lyophilized cells or immobilized cells, can be employed.

In general, any period of time sufficient to produce 2-keto-L-gulonic acid in the culture medium may be used, and the instant process can be conducted by means of a variety of methods. Both microorganisms may be simultaneously inoculated in the medium at the initiation of cultivation. Microorganism (A) may be inoculated first and microorganism (B) subsequently inoculated after a period of cultivation. Both microorganisms may be inoculated separately into respective media, and then (A) is added to (B) or (B) is added to (A) either portionwise or continuously after a period of cultivation, followed by another period of cultivation.

For the process of the present invention, any suitable culturing method may be employed for the microorganisms used as (A) and (B). The method of mixing may be determined in compliance with the properties of the specific microorganism to be employed. The incubation times, inoculation schedules, and ratios of microorganisms (A) and (B) may be optimized for the specific microorganism employed. Namely, the ratio of the amount of microorganism (A) to microorganism (B) and the times of inoculations are preferably selected and determined in view of the growth rate of the respective microorganisms and the L-sorbose producing ability and the ability for converting L-sorbose into 2-keto-L-gulonic acid of the microorganisms involved, and in view of the properties of the media to be used. In some cases, products obtained by treating the cells may also be used as a substitute for either one of the growing cells.

Microorganism (A), which can be employed in the process of the present invention, includes microorganisms which are preserved in a public depository (culture collection) for delivery to any one upon request. One such depositary is the Institute of Fermentation, Osaka, Japan (IFO). The microorganisms are as follows:

Examples for the microorganism (A)

Gluconobacter suboxydans IFO 3130
Gluconobacter suboxydans IFO 3255
Gluconobacter suboxydans IFO 3256
Gluconobacter suboxydans IFO 3257
Gluconobacter suboxydans IFO 3258
Gluconobacter suboxydans IFO 3289
Gluconobacter suboxydans IFO 3290
Gluconobacter suboxydans IFO 3291
Gluconobacter gluconicus IFO 3171
Gluconobacter gluconicus IFO 3285
Gluconobacter gluconicus IFO 3286
Gluconobacter rubiginosus IFO 3244
Gluconobacter albidus IFO 3251
Gluconobacter albidus IFO 3253
Gluconobacter industrius IFO 3261
Gluconobacter cerinus IFO 3262
Gluconobacter cerinus IFO 3263
Gluconobacter cerinus IFO 3265
Gluconobacter cerinus IFO 3266
Gluconobacter cerinus IFO 3267
Gluconobacter cerinus IFO 3270
Gluconobacter diacetonicus IFO 3273
Gluconobacter roseus IFO 3990
Acetobacter aceti subsp. orleans IFO 3259
Acetobacter aceti subsp. aceti IFO 3281
Acetobacter liquefaciens IFO 12257
Acetobacter liquefaciens IFO 12258
Acetobacter liquefaciens IFO 12388
Acetobacter aceti subsp. xylinum IFO 3288
Acetobacter aceti subsp. xylinum IFO 13693
Acetobacter aceti subsp. xylinum IFO 13772
Acetobacter aceti subsp. xylinum IFO 13773

The main identifying characteristics of the microorganism (B), which can be employed in the process of the present invention, are:

Negative oxidase test; ethanol is oxidized to acetic acid; D-glucose is oxidized to D-gluconic acid and 2-keto-D-gluconic acid; ketogenesis of polyalcohols; dihydroxyacetone is not substantially produced from glycerol; 2-keto-D-glucaric acid is produced from D-glucaric acid, but not from D-glucose, D-fructose, D-gluconic acid, D-mannitol or 2-keto-D-gluconic acid; polymorphic apparently no flagella; brown pigments are produced from D-fructose; good growth is observed when co-cultured in the presence of Bacillus megaterium or a cell extract thereof; streptomycin sensitive.

A specific and preferred microorganism which can be used as microorganism (B) was deposited at the Deutsche Sammlung von Mikroorganismen in Goettingen under DSM No. 4025 on Mar. 17, 1987 under the Budapest Treaty (the present address of this institute is: Deutsche Sammlung von Mikroorganismen und Zellkulturen Gmbh, Mascheroder Weg 1b, D-3300 Braunschweig, Federal Republic of Germany). It was designated as a Gluconobacter oxydans microorganism.

Further preferred microorganisms are functional equivalents, subcultures, mutants and variants of the aforementioned microorganisms (A) and (B).

In the preferred embodiment of the present invention, the aforementioned microorganisms (A) and (B) may be inoculated with and cultivated in a medium which includes D-sorbitol. The cells of such microorganisms, for instance, resting cells, or any processed product obtained from the cells may be used to act directly on D-sorbitol. Any techniques and methods for the cultivation of microorganisms may be adopted. The use of aerated and agitated submerged fermenters is particularly preferred. A preferred result may be obtained from cultivation in a liquid broth medium.

As regards the nutrient medium available for the cultivation of the microorganisms (A) and (B), although no special restriction is imposed, an aqueous nutrient medium may include carbon sources and nitrogen sources. Other inorganic salts, small amounts of other nutrients and the like, which can be utilized by the microorganisms, are desirable for the advantageous incubation of the microorganisms. Various nutrient materials which are generally used for the better growth of microorganisms may be included in the medium.

In addition to D-sorbitol used as starting material in the present invention, other substances which are carbon sources may also be added, such as glycerol, D-glucose, D-mannitol, D-fructose, D-arabitol and the like.

Various organic or inorganic substances may also be used as nitrogen sources in the present process, such as meat extract, peptone, casein, corn steep liquor, urea, amino acids, nitrates, ammonium salts and the like. As inorganic substances, magnesium sulfate, potassium phosphate, ferrous and ferric chlorides, calcium carbonate and the like may be used.

The mixing ratio of these nutrients and the amounts of each ingredient may vary with the generic properties of the microorganisms employed, the amounts of the starting material, D-sorbitol, the amount of one of the microorganisms to be inoculated with respect to the other and the times of inoculations, and the other conditions of the incubation which may be selected or determined in accordance with the particulars of the individual case.

The concentration of the starting material, D-sorbitol, in the medium may also be varied with the generic character of the employed microorganisms. D-Sorbitol can be added to the medium at the starting point of cultivation or separately during the cultivation period. In this instant process, the separate addition of D-sorbitol brings about preferable results. A concentration of D-sorbitol of about 20 to 250 g/l in total is generally used and, in particular, a concentration of about 50 to 200 g/l in total.

The conditions of the cultivation may also vary depending on the species and generic character of the microorganisms employed. The composition of the medium may, of course, be selected or determined in accordance with the particulars of the individual case in order to yield the intended product most efficiently, although cultivation temperatures between about 13° and 36° C., preferably between about 18° and 33° C., and a pH value of the medium between about 4.0 and 9.0, preferably between about 6.0 and 8.0, may be maintained. Normally, a cultivation period ranging from 20 to 80 hours is sufficient, and the formation of the intended product in the medium reaches its maximum value within such period.

In order to maintain the pH value of the medium as that most suitable for the enzymatic activity, any suitable acidic or basic agent may be added to the medium in a suitable amount at a suitable time during the cultivation. The same object may alternatively be accomplished by incorporating a suitable buffer or buffering agent into the medium at the beginning of the cultivation.

The 2-keto-L-gulonic acid thus produced in the medium may be separated and purified by conventional methods known in the art, and it may be separated as a salt, e.g. of sodium, potassium, calcium, ammonium or the like. This salt may be converted into a free acid by conventional methods known in the art.

Specifically, the separation may be performed by any suitable combination or repetition of the following steps: by the formation of a salt, by using differences in properties between the product and the surrounding impurities, such as solubility, absorbability and distribution coefficient between the solvents, by adsorption, for example on ion exchange resin. Any of these procedures alone or in combination constitutes a convenient means for isolating the product. The product thus obtained may further be purified in a conventional manner, e.g. by recrystallization or chromatography.

The 2-keto-L-gulonic acid accumulated according to the novel process can easily be isolated, for example, by the following procedure: The supernatant of the culture broth is concentrated after centrifugation under reduced pressure. To the concentrate is added an organic solvent such as ethanol, and the thus obtained 2-keto-L-gulonic acid crystals are separated in the salt form, for example the sodium or calcium salt. Whether the above or other known method is employed, the 2-keto-L-gulonic acid can always easily be isolated.

The 2-keto-L-gulonic acid or its salt thus obtained can be used directly for conversion to L-ascorbic acid by esterification, followed by enolization and lactonization. The 2-keto-L-gulonic acid can be converted to any conventional salt of ascorbic acid.

Culturing methods which can be used include standing cultures, shaking cultures, submerged cultures etc. For mass culture, submerged cultures using batch, fed batch, and continuous operation techniques are of the greatest interest. It is also possible to use the cells of microorganisms (A) and (B) immobilized by well known absorption methods on materials such as cellulose, ceramics or glass beads, etc. and by entrapping methods, e.g. in a gel matrix such as agar, calcium alginate, K-carrageenan and other known polymers. This mode enables the microorganisms to be used repeatedly.

The present invention is illustrated but not limited in any way by the following Examples:

EXAMPLE 1

Strain DSM No. 4025 represents microorganism (B), whereas the microorganisms listed in Table 1 were employed in turn as microorganism (A).

Preparation of Seed Culture

Seed culture was prepared in two different methods as described below.

Method 1: A test tube (18 mm×200 mm) was charged with 5 ml of culture medium (SCM): D-sorbitol 2%, yeast extract (Oriental Yeast) 0.3%, beef extract 0.3%, corn steep liquor 0.3%, polypeptone 1.0%, urea 0.1%, $KH_2PO_4$ 0.1%, $MgSO_4.7H_2O$ 0.02% and $CaCO_3$ 0.1% (pH 7.0 before sterilization) and sterilized by autoclaving at 121° C. for 20 minutes. The test tube was inoculated with one loopful of microorganism (A) and one loopful of microorganism (B), and incubated at 30° C. with shaking (220 rpm) for one day.

Method 2: A test tube (18 mm×200 mm) containing 5 ml of SCM was inoculated with one loopful each of microorganism (B) and microorganism (A) and cultivated at 30° C. with shaking for one day. One drop of the resulting culture was spread on an agar culture medium containing 2% agar in SCM and incubated at 30° C. for 4 days. The microorganisms grown on the agar culture as a mixture were used directly as an inoculum for the following liquid culture. A tube containing 5 ml of SCM was inoculated with a loopful of the mixture described above and incubated at 30° C. with shaking (220 rpm) for one day.

Main Fermentation

Five ml of the resulting individual seed cultures as prepared above was inoculated into a 500 ml of Erlenmeyer flask containing 50 ml of production medium (PM): D-sorbitol 8%, corn steep liquor 1%, urea 1.5%

(sterilized separately), KH$_2$PO$_4$ 0.1%, MgSO$_4$.7H$_2$O 0.01%, CaCO$_3$ 0.6% and antifoam 0.1% (pH 7.0 before sterilization) and incubated at 30° C. for 4 days with shaking (180 rpm). Table 1 summarizes the results of the quantitative determination of 2-keto-L-gulonic acid of the cultured broths as assayed by high performance liquid chromatography.

TABLE 1

| Microorganism (A) | | 2-Keto-L-gulonic acid produced (g/L) Seed culture with | |
|---|---|---|---|
| | | Method 1 | Method 2 |
| Gluconobacter suboxydans | IFO 3255 | 64.1 | 65.2 |
| Gluconobacter suboxydans | IFO 3256 | 51.4 | 56.9 |
| Gluconobacter suboxydans | IFO 3258 | 45.2 | 58.8 |
| Gluconobacter suboxydans | IFO 3289 | 57.1 | 61.8 |
| Gluconobacter suboxydans | IFO 3290 | 11.4 | 65.9 |
| Gluconobacter suboxydans | IFO 3291 | 63.7 | 64.9 |
| Gluconobacter gluconicus | IFO 3171 | 46.9 | 58.9 |
| Gluconobacter gluconicus | IFO 3285 | 67.8 | 69.1 |
| Gluconobacter gluconicus | IFO 3286 | 59.9 | 26.4 |
| Gluconobacter albidus | IFO 3251 | 5.1 | 55.6 |
| Gluconobacter albidus | IFO 3253 | 53.4 | 55.6 |
| Gluconobacter cerinus | IFO 3263 | 56.0 | 38.2 |
| Gluconobacter cerinus | IFO 3265 | 44.9 | 26.1 |
| Gluconobacter cerinus | IFO 3267 | 58.6 | 58.0 |
| Gluconobacter cerinus | IFO 3270 | 59.3 | 28.3 |
| Acetobacter liquefaciens | IFO 12258 | 27.9 | 9.6 |
| Acetobacter liquefaciens | IFO 12388 | 25.0 | 18.9 |
| Acetobacter aceti subsp. xylinum | IFO 3288 | 32.6 | 35.2 |
| None | | 2.1 | 1.7 |

EXAMPLE 2

Seed cultures of Gluconobacter suboxydans IFO 3255 and the strain DSM No. 4025 were prepared in the same manner as described in the method 1 in Example 1. The cell concentrations of the seed cultures of Gluconobacter suboxydans IFO 3255 and the strain DSM No. 4025 were 3.7×10$^{10}$ cells/ml and 5.4×10$^8$ cells/ml, respectively. The each resulting seed culture was inoculated into 50 ml of PM in 500 ml of Erlenmeyer flask at total inoculum size of 10% (v/v), where the inoculum ratio (%, v/v) between Gluconobacter suboxydans IFO 3255 and the strain DSM No. 4025 was varied: 0:10, 1:9, 2:8, 3:7, 4:6, 5:5, 6:4, 7:3, 8:2, 9:1 and 10:0. The flasks were incubated at 30° C. for 4 days. The results are shown in Table 2. When the inoculum ratio of the strain DSM No. 4025 and Gluconobacter suboxydans IFO 3255 was between 1:9 and 4:6, 2-keto-L-gulonic acid was produced over the range of between 63.9 g/l and 66.6 g/l from 80 g/l of D-sorbitol (conversion ratio: 74.9 to 78.1 mol %) without any 2-keto-D-gluconic acid accumulation.

TABLE 2

| Inoculum ratio of The microorganism (A)[1]: The microorganism (B)[2] | Amount produced (g/L) | | |
|---|---|---|---|
| | 2-KGA[3] | 2-KD[4] | L-Sorbose |
| 10:0 | 0 | 0 | 73.7 |
| 9:1 | 63.9 | 0 | 0 |
| 8:2 | 66.6 | 0 | 0 |
| 7:3 | 65.9 | 0 | 0 |
| 6:4 | 64.5 | 0 | 0 |
| 5:5 | 59.2 | 2.2 | 0 |
| 4:6 | 63.1 | 1.6 | 0 |
| 3:7 | 18.9 | 18.9 | 0 |
| 2:8 | 6.7 | 18.3 | 0 |
| 1:9 | 5.2 | 19.1 | 0 |

TABLE 2-continued

| Inoculum ratio of The microorganism (A)[1]: The microorganism (B)[2] | Amount produced (g/L) | | |
|---|---|---|---|
| | 2-KGA[3] | 2-KD[4] | L-Sorbose |
| 0:10 | 1.1 | 8.4 | 0 |

Remarks:
[1]Gluconobacter suboxydans IFO 3255
[2]The strain DSM No. 4025
[3]2-Keto-L-gulonic acid
[4]2-Keto-D-gluconic acid

EXAMPLE 3

Gluconobacter suboxydans IFO 3255 and Gluconobacter gluconicus IFO 3285 were used as microorganism (A), and the strain DSM No. 4025 was used as microorganism (B). An individual seed culture (200 ml) was prepared in a similar manner as the method 2 described in Example 1. The individual seed culture (200 ml) was inoculated into a 3-L fermenter containing about 1.7 L of the fermentation medium: D-sorbitol 8%, 10%, or 12%, yeast extract 0.5%, corn steep liquor 2.5%, MgSO$_4$.7H$_2$O 0.0086%, urea 0.086% (sterilized separately), KH$_2$PO$_4$ 0.086% and antifoam 0.15%, sterilized at 121° C. for 20 minutes. After the inoculation, the culture volume was adjusted to 2 L by the addition of sterilized water. The fermentation was carried out at 30° C., 700 rpm for agitation and 1 l/min for aeration. The pH of the culture was maintained at 7.0 with 4N-Na$_2$CO$_3$. The results are shown in Table 3.

TABLE 3

| Microorganism (A) | Initial D-sorbitol concentration (%) | Amount produced (g/L) | | |
|---|---|---|---|---|
| | | 2-KGA[1] | 2-KD[2] | L-Sorbose |
| Gluconobacter suboxydans IFO 3255 | 8 | 65.3 | 0 | 0 |
| | 10 | 77.1 | 0 | 0 |
| | 12 | 81.3 | 0 | 11.6 |
| Gluconobacter gluconicus IFO 3285 | 8 | 66.4 | 0 | 0 |
| | 10 | 62.8 | 0 | 0 |
| | 12 | 61.5 | 1.8 | 29.6 |

Remarks:
[1]2-Keto-L-gulonic acid
[2]2-Keto-D-gluconic acid

EXAMPLE 4

In the same manner as described in Example 3, the seed culture (200 ml) of the mixture of Gluconobacter suboxydans IFO 3255 and the strain DSM No. 4025 was inoculated into 3-L fermenter containing 8% D-sorbitol in the fermentation medium and the working volume was adjusted to 2 L with sterilized water. The fermentation was started under the same conditions as described in Example 3. Separately, a 500 ml medium bottle charged with 300 ml of feeding medium: 120 g of D-sorbitol, 10 g of yeast extract, 50 g of corn steep liquor, 0.172 g of KH$_2$PO$_4$, 1.72 g of urea (sterilized separately) and 2.5 g of antifoam, was prepared. During the fermentation, the above feeding medium was continuously fed to the fermenter at the rate of 15 ml/hr between the fermentation period of 12 and 18 hours, 60 ml/hr between that of 18 hours and 21 hours and 4.3 ml/hr between that of 21 hours and 28 hours by using a peristaltic pump. As a result, 224 g of 2-keto-L-gulonic acid was produced from 276 g of D-sorbitol at the conversion yield of 76.1 mol % in 51 hours fermentation.

EXAMPLE 5

One loopful of Gluconobacter suboxydans IFO 3255 was inoculated into 500 ml Erlenmeyer flask containing 100 ml of SCM and incubated at 30° C. for one day. The 10 ml of the culture thus obtained was transferred into 500 ml Erlenmeyer flask containing 100 ml of SCM and incubated at 30° C. for one day. In total, 1.5 L of the seed culture of Gluconobacter suboxydans IFO 3255 was prepared. One loopful of the strain DSM No. 4025 was inoculated into 500 ml Erlenmeyer flask containing 100 ml of the seed culture medium: L-sorbose 8%, glycerol 0.05%, urea 0.5% (sterilized separately), corn steep liquor 1.75%, baker's yeast (Oriental Yeast) 5.0%, $MgSO_4.7H_2O$ 0.25%, $CaCO_3$ 1.5% and antifoam 0.1% (pH 7.0 before sterilization) and incubated at 30° C. for one day on a rotary shaker (180 rpm). A 10 ml of the culture thus prepared was inoculated into the 100 ml of the same medium as above and incubated for one day at 30° C. In total, 1.5 L of the seed culture of the strain DSM No. 4025 was prepared. Into a 50-L fermenter, 25 L of the fermentation medium D-sorbitol 8%, corn steep liquor 0.5%, $MgSO_4. 7H_2O$ 0.01%, $KH_2PO_4$ 0.025% and antifoam 0.17% were added and sterilized at 121° C. for 30 minutes. Both of the seed cultures (1.5 L each) were inoculated simultaneously, and total culture volume was adjusted to 30 L by the addition of sterilized water. The fermentation was carried out at 30° C., 400 rpm for agitation and 20 L/min for aeration. The pH of the culture was maintained at 7.0 with 6.25 N-NaOH. Separately, a 5-L medium bottle was charged with 4 L of a feeding medium containing 1,800 g of D-sorbitol, 150 g of corn steep liquor, 1.29 g of $MgSO_4.7H_2O$, 7.5 g of $KH_2PO_4$ and 25 g of antifoam was sterilized at 120° C. for 20 minutes. After 12 hours cultivation, the feeding medium was continuously fed to the fermenter at the rate of 222 ml/hr for 18 hours by using a peristaltic pump. After 45.5 hours cultivation, 36.8 L of fermentation broth containing 93.5 g/L of 2-keto-L-gulonic acid was obtained. In other words, 3,441 g of 2-keto-L-gulonic acid were produced from 4,200 g of D-sorbitol with the conversion yield of 76.8 mol %.

EXAMPLE 6

The fermentation broth (36.8 L) obtained in Example 5 was centrifuged to remove the cellular and other sediment. The supernatant (2 L) containing 93.5 g/L of 2-keto-L-gulonic acid was concentrated under reduced pressure at 45° C. to about 1 L. During the concentration, the white precipitates were observed. Then the concentrate was added by 100 ml of ethanol and allowed to stand at 10° C. for one day. Resulting precipitates were collected by filtration, washed with a small amount of 50% cold ethanol and dried over at room temperature under reduced pressure. As a result, 137.6 g of monosodium 2-keto-L-gulonic acid monohydrate were obtained with the purity of 99.14% as the first crop. The mother liquor was concentrated under reduced pressure to about 400 ml, added by about 100 ml of ethanol, allowed to stand at 10° C. for 24 hours. As a result, 71.9 g of monosodium 2-keto-L-gulonic acid monohydrate (purity: 85.04%) were obtained as the second crop.

EXAMPLE 7

The supernatant (0.5 L) as obtained in Example 6 was passed through Amberlite IR-120(H-type)(Rohm and Haas Company) and dried under reduced pressure. To the dried material (about 50 g), 400 ml of methanol and 0.5 ml of 98% sulfuric acid were added. After the mixture was heated at 90° C. for 2 hours, methanol was removed and the residue was washed with a small amount of methanol and dried up. The dried residue was then suspended into 150 ml of methanol and refluxed with 10 g of sodium methylate under heating. Resulting crystals after cooling were filtered out and dried under reduced pressure. As a result, 35.1 g of soidum L-ascorbic acid were obtained.

EXAMPLE 8

One loopful of Gluconobacter suboxydans IFO 3291 was inoculated into a 500 ml Erlenmeyer flask containing 100 ml of SCM and incubated at 30° C. for 18 hours. One loopful of the strain DSM No. 4025 was inoculated into a 500 ml Erlenmeyer flask containing 100 ml of the seed culture medium as described in Example 5 and incubated at 30° C. for 22 hours. The 10 ml of the culture thus prepared were inoculated into a 500 ml Erlenmeyer flask containing 100 ml of the same medium as above and incubated for 18 hours at 30° C.

Into a 3-L fermenter, 1.6 liters of the fermentation medium containing 160 g of D-sorbitol, 10 g of corn steep liquor, 0.2 g of $MgSO_4.7H_2O$, 0.5 g of $KH_2PO_4$ and 2 g of antifoam were added and sterilized at 121° C. for 30 minutes.

Both of the seed cultures (100 ml each) as prepared above were inoculated simultaneously, and the total culture volume was adjusted to 2 liters by the addition of sterilized water. Separately, a 500 ml medium bottle was charged with 300 ml of feeding medium containing 180 g of D-sorbitol, 10 g of corn steep liquor, 0.086 g of $MgSO_4.7H_2O$, 0.215 g of $KH_2PO_4$ and 1 g of antifoam was sterilized at 121° C. for 30 minutes. The fermentation was conducted with an aeration rate of 1.0 L/minute and the pH of the medium adjusted at 7.0 by using NaOH. The other fermentation parameters are given in Table 4. After 6.5 hours of cultivation, the feeding medium was continuously fed to the fermentor at the rate of 30 ml/hour for 10 hours by using a peristaltic pump. As shown in Table 4, 322.7 g of 2-keto-L-gulonic acid in total was produced from 340 g of D-sorbitol used with the molar conversion yield of 89.0%, when the fermentation was conducted at 28° C. with an agitation speed of 800 rpm.

TABLE 4

| Fermentation conditions | | 2-Keto-L-gulonic acid produced (g) | Molar conversion yield (mol %) |
| --- | --- | --- | --- |
| Temperature (°C.) | Agitation (rpm) | | |
| 28 | 800 | 322.7 | 89.0 |
| 30 | 700 | 307.6 | 84.9 |

Remark: 340 g of D-sorbitol was used in total.

Additional deposits under the Budapest treaty were effected as per Mar. 30, 1992 concerning particular strains and mixtures of strains respectively as made use of in the Examples as follows:

| | | New Deposit No. |
| --- | --- | --- |
| A Single culture strain DSM No. 4025 | | FERM BP-3812 |
| B Mixed microorganism cultures | Deposit No. | |
| strain DSM No. 4025 + | Gluconobacter suboxydans IFO 3256 | FERM BP-3815 |

| | | New Deposit No. |
|---|---|---|
| strain DSM No. 4025 + | Gluconobacter suboxydans IFO 3291 | FERM BP-3813 |
| strain DSM No. 4025 + | Gluconobacter suboxydans IFO 3255 | FERM BP-3814 |

We claim:

1. A process for producing 2-keto-L-gulonic acid which comprises:
   (a) culturing a mixture of microorganisms in a medium containing D-sorbitol, the first of said microorganisms being a Gluconobacter or Acetobacter which converts D-sorbitol to L-sorbose and which does not convert D-sorbitol to 2-keto-L-gulonic acid, and the second of said microorganisms being a Gluconobacter oxydans having identifying characteristics of strain DSM 4025 and which converts D-sorbitol to 2-keto-L-gulonic acid in substantially lower amounts than it converts L-sorbose to 2-keto-L-gulonic acid, said culturing being carried out for a sufficient period of time to produce 2-keto-L-gulonic acid; and
   (b) recovering 2-keto-L-gulonic acid from said medium.

2. The process of claim 1 which comprises recovering 2-keto-L-gulonic acid as a salt thereof from said medium.

3. A process of claim 1 wherein the yield of 2-keto-L-gulonic acid produced in the medium is from at least 60 grams per liter of medium at the molar conversion yield of 70% to 130 grams per liter of medium at the molar conversion yield of 89%.

4. A process of claim 1 wherein the yield of 2-keto-L-gulonic acid produced in the medium is from at least 130 grams per liter of medium at the molar conversion yield of 89%.

5. A process of claim 1, wherein the first microorganism belongs to the species Gluconobacter suboxydans, Gluconobacter gluconicus, Gluconobacter rubiginosus, Gluconobacter albidus, Gluconobacter industrius, Gluconobacter cerinus, Gluconobacter diacetonicus, Gluconobacter roseus, Acetobacter aceti subsp. orleans, Acetobacter liquefaciens or Acetobacter aceti subsp. xylinum.

6. A process of claim 1 wherein the first microorganism is a Gluconobacter of the strain IFO 3255, 3256, 3258, 3267, 3285, 3290 or 3291.

7. A process of claim 1 wherein the second microorganism corresponds to strain DSM No. 4025.

8. A process of claim 1 wherein D-sorbitol is present in the medium at a concentration of from about 20 grams to about 250 grams per liter of medium.

9. A process of claim 8 wherein the concentration of D-sorbitol is from about 50 grams to about 200 grams per liter of medium.

10. A process of claim 1 wherein the culturing is carried out at a pH between about 4.0 and about 9.0.

11. A process of claim 10 wherein the culturing is carried out at a pH of between about 6.0 and about 8.0.

12. A process of claim 1 wherein the culturing is carried out at a temperature between about 13° C. and 36° C.

13. A process of claim 12 wherein the temperature is between about 18° C. and 33° C.

14. A process of claim 1 wherein the 2-keto-L-gulonic acid is reacted to L-ascorbic acid or a salt thereof.

15. A process of claim 1 wherein the first microorganism is Gluconobacter suboxydans IFO 3255 and the second microorganism is DSM No. 4025.

16. A process of claim 15 wherein the inoculum ratio (%, v/v) of the first microorganism to the second microorganism is between 1:9 and 4:6.

17. A process of claim 1 wherein the first microorganism is Gluconobacter suboxydans IFO 3256 and the second microorganism is DSM No. 4025.

18. A process of claim 1 wherein the first microorganism is Gluconobacter suboxydans IFO 3291 and the second microorganism is DSM No. 4025.

* * * * *